US00PP11069P

United States Patent [19]

Plate

[11] Patent Number: Plant 11,069

[45] Date of Patent: Sep. 28, 1999

[54] SINNINGIA PLANT NAMED 'GLO PINK'

[75] Inventor: Renate Plate, Bremen, Germany

[73] Assignee: Wolfgang Bock Pflanzenexport KG, Bremen, Germany

[21] Appl. No.: 08/933,398

[22] Filed: Sep. 19, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—Foley & Lardner

[57] ABSTRACT

A new and distinct variety of *Sinningia×hybrida* plant named 'Glo Pink', particularly characterized by its very large multicolor pink, velvet textured double flowers clustered in the center of the plant. The plants grow very quickly, becoming marketable in approximately 12 weeks, and are very floriferous, often having 4–6 flowers open at a given time.

1 Drawing Sheet

The present invention comprises a new and distinct cultivar of *Sinningia×hybrida,* a genus in the family Gesneriaceae, and referred to by the cultivar name 'Glo Pink'. The new cultivar is a hybrid selected from the progeny of a cross of parent plants identified below.

Hybrids of *Sinningia speciosa*, or Gloxinia as they are commonly known, are popular potted plants which may be cultivated indoors or in greenhouses. They are distinguished by their large, showy velvet textured flowers which come in various shades of violet, rose, red, or white.

Sinningia are typically propagated from seeds, or by leaf cuttings or tissue culture. The new cultivar is a sterile hybrid which does not produce any seeds and is asexually propagated by tissue culture.

The new cultivar is a product of a breeding program carried out by the inventor Renate Plate in Bremen, Germany. The new cultivar named 'Glo Pink' is a result of several generations of crosses of selected, but unnamed *Sinningia speciosa* beginning in 1994. The new cultivar 'Glo Pink' was discovered by the inventor from the progeny of the stated cross in Bremen, Germany by Renate Plate in 1995. Asexual propagation by tissue culture done under the supervision of the inventor in laboratories in Bremen, Germany was used to increase the number of plants for evaluation and has demonstrated the stability of the plant from generation to generation.

The following observations, measurements and values describe plants grown in Apopka, Fla. in greenhouse conditions which are typical of those generally used in horticultural practice.

The following traits have been repeatedly observed to be characteristics which in combination distinguish 'Glo Pink' from generally available seedling-derived Sinningia common in commercial cultivation.

1. The flowers produced by 'Glo Pink' are double, very large, multicolor pink, and are clustered in the center of the plant.

2. Plants of 'Glo Pink' have a compact growth habit, and are suitable for cultivation in 10–15 cm pots.

3. Plants of 'Glo Pink' are very floriferous, typically having 4–6 flowers open at a given time, and 10 or more buds in various stages of development and which open in succession. Once in bloom, the plant typically remains in bloom for 12 weeks.

4. Plants of 'Glo Pink' grow very quickly, producing marketable flowering plants in approximately 12 weeks.

It is difficult to compare the new cultivar with seed-derived Sinningia which are heterogeneous genetically, and therefore lack uniformity in flower color and quality. By comparison, 'Glo Pink' is a single superior genotype asexually propagated preferably by tissue culture. Thus, its combined horticultural properties listed above are uniform and predictable.

All color references are measured against The Royal Horticultural Society color chart. Colors are approximate as color depends on horticultural practices such as light level and fertilization rate, among others, without, however, any change in genotype.

The color photographic drawing comprises a top perspective view of the flowers and foliage of a plant of 'Glo Pink' grown in a 15 cm pot. The photograph was taken approximately 16 weeks after planting a small cutting obtained by tissue culture and grown under appropriate growing conditions.

Colors are as accurate as possible with color illustrations of this type.

Origin: Seedling from a cross of selected, but unnamed *Sinningia speciosa.*

Classification: *Sinningia×hybrida,* cv, 'Glo Pink'.

Propagation: Asexual propagation by tissue culture or leaf cuttings.

Flowers:

*Calyx.*—6–7 lobed, lobes lanceolate, acutely tapered. Approximately 3.0 cm to 3.4 cm long, and 1.0 cm to 1.4 cm wide. Adaxial color is greener than, but closest to 146 A–B; abaxial color is 146 C.

*Corolla.*—Campanulate, outermost whorl has approximately 6 lobes. Secondary inner whorls of corolla are ruffled and convoluted in appearance. The number of lobes is variable, 7 to 9. Corolla approximately 5.8 cm to 6.2 cm long, and 9.0 cm to 10.3 cm in diameter. The adaxial color of the lobes when fully open is 62 D, variably marked with 63 B–C. The junction of the tube and the lobes is 63 A–B. The tube of the corolla is 71 B striated with 71 A. The base of the tube is speckled with 59 A. The secondary inner whorls of the corolla have markings on both surfaces which are similar to those on the adaxial surface of the outermost whorl of the corolla. The abaxial color of the lobes is 62 D, variably marked with 63 B–C, with areas of 146 D. The corolla darkens to 165 B with senescence.

*Peduncle.*—Approximately 9.8 cm to 11.4 cm long, and 5 mm to 6 mm in diameter measured at the midpoint between the calyx and the stem. Color is 146 D, lightly flushed with 183 B.

*Bud.*—Tightly folded, enclosed in the calyx, round, 0.8–1.5 cm in width, light green in color, R.H.S. 147

C–D, but it rapidly expands and partially opens/unfolds to take on the colors of the mature flower.

*Flowering habit.*—Flowers borne singularly, carried above the foliage, one flower per stem; frequently there are two flower stems per leaf node.

*Arrangement of flowers.*—The flowers are clustered together above the foliage in the center of the plant.

*Texture of flowers.*—Thick and velvety in appearance.

*Quantity of bloom.*—Plants of 'Glo Pink' are very floriferous, typically having 4–6 flowers open at a given time, and 10 or more buds in various stages of development and which open in succession.

*Duration of bloom.*—Once in bloom, the plant typically remains in bloom for approximately 12 weeks. Individual flowers remain open for approximately 14 days before senescing.

*Fragrance.*—None.

*Reproductive organs.*—Stamens and anthers are reduced and petaloid; style and stigma are misshapen and frequently petaloid, variable in size and 155 D in color. Ovary is reduced in size. Seed characteristics— Sterile hybrid.

Plant:

*Form.*—Basal rosettes of rugose velvet texture; elliptic, paired, opposite leaves arranged around short stems.

*Height.*—approximately 19 cm to 20.5 cm including flowers.

*Diameter.*—Approximately 36 cm to 39.5 cm.

*Stems.*—approximately 0.9 cm to 1.5 cm diameter; internodes approximately 1.1 cm to 1.4 cm; color is 146 C–D, lightly flushed with 183 B.

*Resistance to pests and disease.*—Typical, no special observations made.

Foliage:

*Size of leaf.*—The largest leaves are approximately 17 cm to 18.5 cm long, and 14.8 cm to 15.5 cm wide. Average sized leaves are approximately 12.5 cm to 13.4 cm long, and 9.9 cm to 11.6 cm wide.

*Shape of leaf.*—The leaf blade is ovate with an obtuse to cordate base and an obtuse to acute tip. The leaf petioles are approximately 4.0 cm to 5.0 cm long and 0.8 cm in diameter measured at the midpoint between the stem and the leaf. The leaf margins are crenate, and somewhat wavy. The leaf blade may be flat or cupped.

*Surface texture.*—The upper surfaces of the leaf are rugose and pubescent. The veins and midrib are sunken on the upper surface, and protruding on the lower surface. The color of the veins and midrib is 146 D on the adaxial surface and 148 C–D on the abaxial surface.

*Color.*—The leaves are dark green throughout, with the adaxial surface being 139 A and the abaxial surface 148 C–D. The petioles are 146 D.

Roots: Stems arise from a fleshy tuber which is approximately 2.0 cm to 3.0 cm in diameter at the time of flowering. The tuber is brownish white, and has numerous greenish white to brown fibrous roots.

I claim:

1. A new and distinct cultivar of *Sinningia×hybrida* plant named 'Glo Pink', as illustrated and described.

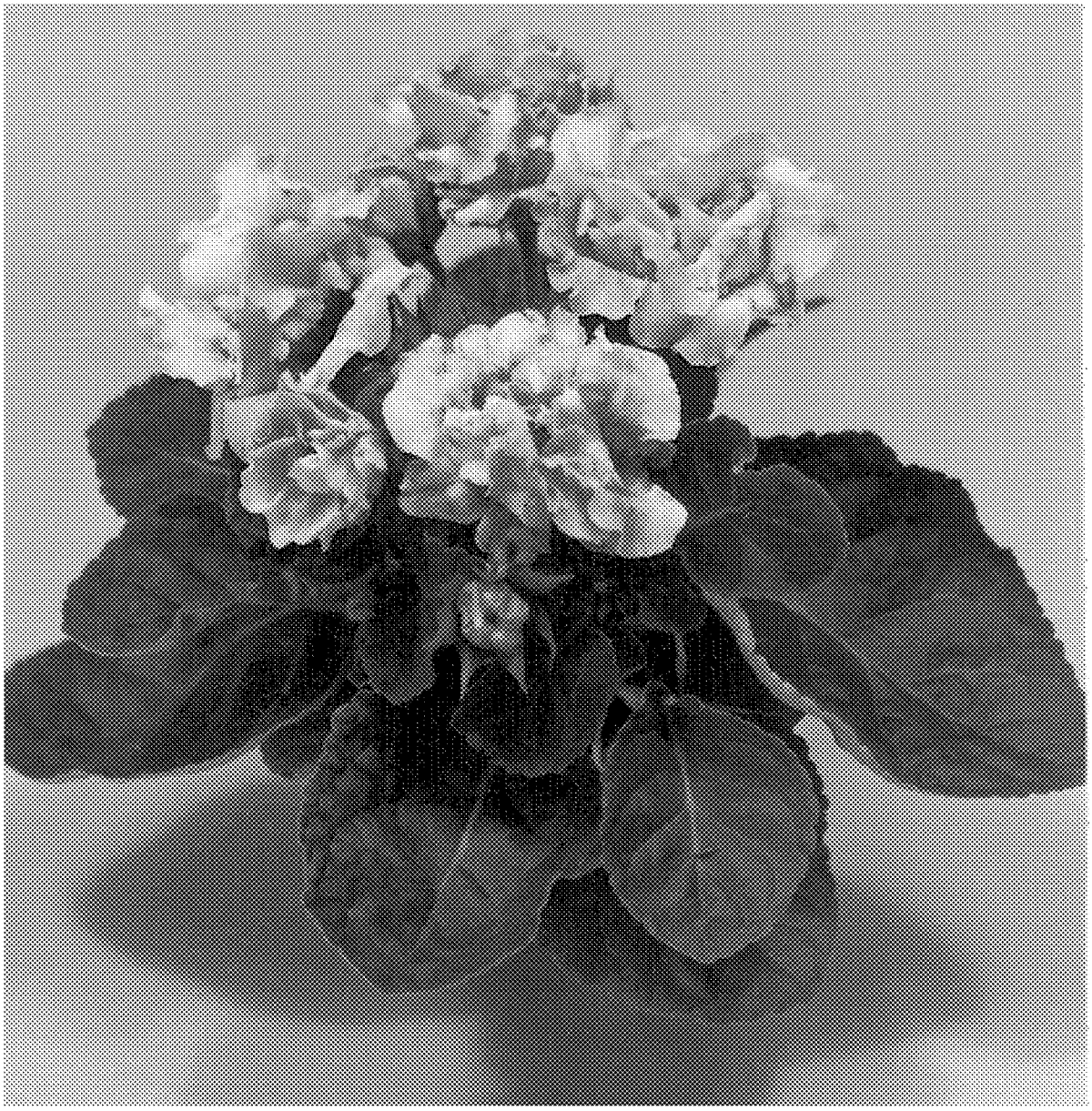

* * * * *